United States Patent
Heischkel et al.

(10) Patent No.: US 8,044,197 B2
(45) Date of Patent: *Oct. 25, 2011

(54) RADIATION CURABLE 1,3,5-TRIAZINE CARBAMATES AND 1,3,5-TRIAZINE UREAS CONTAINING VINYL GROUPS, METHACRYLOYL GROUPS, OR ACRYLOYL GROUPS

(75) Inventors: Yvonne Heischkel, Mannheim (DE); Joerg Schneider, Weinheim (DE); Reinhold Schwalm, Wachenheim (DE); Guenter Scherr, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 834 days.

This patent is subject to a terminal disclaimer.

(21) Appl. No.: 10/593,316

(22) PCT Filed: Apr. 8, 2005

(86) PCT No.: PCT/EP2005/003687
§ 371 (c)(1),
(2), (4) Date: Sep. 18, 2006

(87) PCT Pub. No.: WO2005/103016
PCT Pub. Date: Nov. 3, 2005

(65) Prior Publication Data
US 2007/0208101 A1 Sep. 6, 2007

(30) Foreign Application Priority Data
Apr. 14, 2004 (DE) .......................... 10 2004 018 546

(51) Int. Cl.
*C07D 251/70* (2006.01)
*C08F 2/00* (2006.01)
*C08G 18/02* (2006.01)
*C08G 18/68* (2006.01)

(52) U.S. Cl. .......................... 544/196; 544/200; 524/100
(58) Field of Classification Search .................. 544/196, 544/200, 197; 524/100; 514/100
See application file for complete search history.

(56) References Cited

U.S. PATENT DOCUMENTS

| 7,169,923 B2 * | 1/2007 | Schneider et al. | 544/196 |
| 7,371,856 B2 * | 5/2008 | Schneider et al. | 544/196 |
| 7,507,818 B2 * | 3/2009 | Schneider et al. | 544/196 |
| 7,517,474 B2 * | 4/2009 | Wagner et al. | 252/401 |

FOREIGN PATENT DOCUMENTS

| DE | 101 51 564 | 4/2003 |
| EP | 0 305 115 | 3/1989 |
| EP | 0 359 430 | 3/1990 |
| EP | 0 366 884 | 5/1990 |
| EP | 0 473 948 | 3/1992 |
| JP | 2003 280187 | 10/2003 |
| WO | 97 08235 | 3/1997 |

OTHER PUBLICATIONS

Keher et al., "THIOL/ENE Curable Polymer Technology", American Chemical Socieity, Division of Organic Coatings and Plastics Chemistry, vol. 33, No. 1, pp. 295-302, 1973 (English abstract only).
U.S. Appl. No. 12/439,928, filed Mar. 4, 2009, Dylllick-Brenzinger, et al.

* cited by examiner

*Primary Examiner* — Venkataraman Balasubramanian
(74) *Attorney, Agent, or Firm* — Oblon, Spivak, McClelland, Maier & Neustadt, L.L.P.

(57) ABSTRACT

Radiation-curable 1,3,5-triazine carbamates and 1,3,5-triazine ureas, processes for preparing them and their use.

26 Claims, No Drawings

RADIATION CURABLE 1,3,5-TRIAZINE CARBAMATES AND 1,3,5-TRIAZINE UREAS CONTAINING VINYL GROUPS, METHACRYLOYL GROUPS, OR ACRYLOYL GROUPS

The present invention relates to radiation-curable 1,3,5-triazine carbamates and 1,3,5-triazine ureas, to processes for preparing them, and to their use.

The preparation of 1,3,5-triazine carbamates is described in DE-A1 101 51 564 or WO 97/08235, p. 3 lines 9-22. The preparation routes specified therein lead to alkyl-substituted 1,3,5-triazine carbamates. The strongly basic reaction medium makes these methods unsuitable for functional groups such as ester or carbamate groups.

EP-A2 305 115 describes radiation-activable 1,3,5-triazine compounds which comprise at least one halogenated group $CX_3$ and via UV exposure are able photochemically to initiate a free-radical addition polymerization. The triazine compounds may further comprise free-radically polymerizable groups, e.g., hydroxyethyl acrylate, attached via a urethane group.

EP-A 359 430 likewise describes halogenated 1,3,5-triazine compounds which simultaneously comprise a free-radically polymerizable group. Compounds of this kind form free radicals under the influence of light.

The radiation-activable halogen groups in these systems have an adverse effect on the UV stability of compounds or coatings which comprise them, and consequently may lead for example to the yellowing of coatings.

EP-A 366 884 describes 1,3,5-triazine compounds which comprise at least two vinyl-terminated groups and at least one carbamyl group. These 1,3,5-triazine compounds comprise reaction products of melamine with aldehydes, especially with formaldehyde. Besides the vinyl end groups, the 1,3,5-triazine compounds comprise methylol and/or alkylated methylol groups.

A similar system is described in EP-A 473 948. It comprises substituted 1,3,5-triazines which are obtained by condensing melamine with formaldehyde and comprise ethylenically unsaturated groups.

Systems of this kind are sensitive to acid because of their aminal or N,O-acetal structure.

It was an object of the present invention to provide halogen-free, radiation-curable 1,3,5-triazine carbamates and 1,3,5-triazine ureas which as far as possible ought also to have dual-cure capability.

This object is achieved by means of 1,3,5-triazine carbamates and 1,3,5-triazine ureas of formula (I)

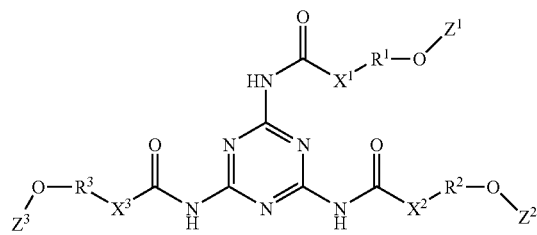

in which
$R^1$, $R^2$ and $R^3$ each independently of one another are a divalent organic radical,
$X^1$, $X^2$ and $X^3$ each independently of one another are oxygen or substituted or unsubstituted nitrogen (NR),
R being hydrogen or $C_1$-$C_{20}$ alkyl, and
$Z^1$, $Z^2$ and $Z^3$ each independently of one another are vinyl, methacryloyl or acryloyl.

The present invention further provides 1,3,5-triazine carbamates and 1,3,5-triazine ureas of formula (II)

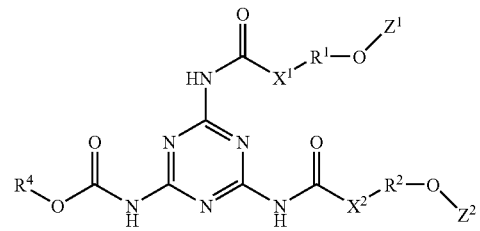

and of formula (III)

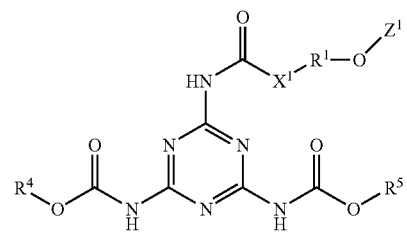

in which
$X^1$, $X^2$, $Z^1$, $Z^2$, $R^1$ and $R^2$ are as defined above and
$R^4$ and $R^5$ each independently of one another are $C_1$-$C_4$ alkyl.

The present invention additionally provides isocyanato-functional 1,3,5-triazine carbamates and 1,3,5-triazine ureas of formula (V)

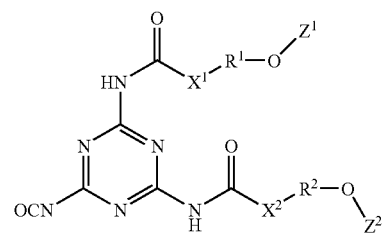

and formula (VI)

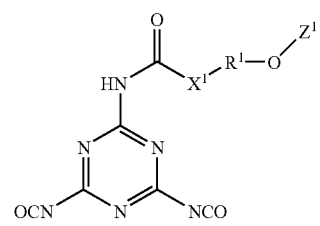

In which
$X^1$, $X^2$, $Z^1$, $Z^2$, $R^1$ and $R^2$ are as defined above.

The present invention also provides processes for preparing these compounds.

Radiation-curable 1,3,5-triazine carbamates and 1,3,5-triazine ureas of the invention are obtainable by reacting compounds of formula (IV)

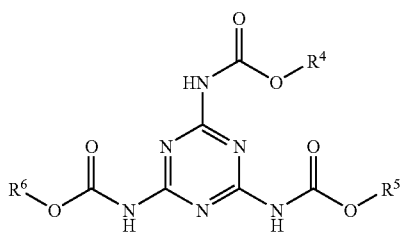

in which
R⁴, R⁵ and R⁶ each independently of one another can be $C_1$-$C_4$ alkyl
with compounds containing a hydroxyl or amino group and at least one vinyl, methacryloyl or acryloyl group.

Alternatively the compounds of formulae (I), (II) and (III) are preparable by reacting 2,4,6-triisocyanato-1,3,5-triazine with alcohols or amines of formula (VII) and, in the case of compounds (II) and (III), by simultaneous, prior or subsequent reaction with alcohols of the formula R⁴OH or R⁵OH.

Compounds of formulae (V) or (VI) are preparable by reacting 2,4,6-triisocyanato-1,3,5-triazine with alcohols or amines of formula (VII).

In the above definitions, divalent organic radicals are preferably $C_1$-$C_{20}$ alkylene, $C_3$-$C_{12}$ cycloalkylene or $C_6$-$C_{12}$ arylene unsubstituted or substituted by $C_1$-$C_8$ alkyl, $C_2$-$C_8$ alkenyl, carboxyl, carboxy-$C_1$-$C_8$ alkyl, $C_1$-$C_{20}$ acyl, $C_1$-$C_8$ alkoxy, $C_6$-$C_{12}$ aryl, hydroxyl or hydroxy-substituted $C_1$-$C_8$-alkyl, or are $C_2$-$C_{20}$ alkylene interrupted by one or more oxygen and/or sulfur atoms and/or by one or more substituted or unsubstituted imino groups and/or by one or more —(CO)—, —O(CO)O—, —(NH)(CO)O—, —O(CO)(NH)—, —O(CO)— or —(CO)O— groups.

In these definitions
$C_6$-$C_{12}$ arylene substituted by $C_1$-$C_8$ alkyl, $C_2$-$C_8$ alkenyl, carboxyl, carboxy-$C_1$-$C_8$ alkyl, $C_1$-$C_{20}$ acyl, $C_1$-$C_8$ alkoxy, $C_6$-$C_{12}$ aryl, hydroxyl or hydroxy-substituted $C_1$-$C_8$ alkyl is for example 1,2-, 1,3- or 1,4-phenylene, 4,4'-biphenylene and also 1',4-tolylene, 1',1'-dimethyl-1',4-tolylene, 2,4-dimethylphenyl-1',1''-ene or 1',1'-dimethyl-2,4-dimethylphenyl-1',1''-ene, $C_3$-$C_{12}$ cycloalkylene substituted by $C_1$-$C_8$ alkyl, $C_2$-$C_8$ alkenyl, carboxyl, carboxy-$C_1$-$C_8$ alkyl, $C_1$-$C_{20}$ acyl, $C_1$-$C_8$ alkoxy, $C_6$-$C_{12}$ aryl, hydroxyl or hydroxy-substituted $C_1$-$C_8$-alkyl is for example cyclopropylene, 1,2- or 1,3-cyclopentylene, 1,2-, 1,3- or 1,4-cyclohexylene, 3,5,5-trimethyl-1,3-cyclohexylene, cyclooctylene or cyclododecylene, $C_1$-$C_{20}$ alkylene substituted by $C_1$-$C_8$ alkyl, $C_2$-$C_8$ alkenyl, carboxyl, carboxy-$C_1$-$C_8$ alkyl, $C_1$-$C_{20}$ acyl, $C_1$-$C_8$ alkoxy, $C_6$-$C_{12}$ aryl, hydroxyl or hydroxy-substituted $C_1$-$C_8$ alkyl is for example 1,2-ethylene, 1,2-propylene, 1,3-propylene, 1,4-butylene, 1,6-hexylene, 1,1-dimethyl-1,2-ethylene, 2-methyl-1,3-propylene, 2,2-dimethyl-1,3-propylene or 2,2-dimethyl-1,4-butylene, $C_2$-$C_{20}$ alkylene interrupted by one or more oxygen and sulfur atoms and/or one or more substituted or unsubstituted imino groups and/or by one or more —(CO)—, —O(CO)O—, —(NH)(CO)O—, —O(CO)(NH)—, —O(CO)— or —(CO)O— groups is for example 3-aza-1,5-pentylene, 3-methyl-3-aza-1,5-pentylene, 3,6-diaza-1,8-octylene, 3,6,9-triaza-1,11-undecylene, 3-oxa-1,5-pentylene, 3,6-dioxa-1,8-octylene or 3,6,9-trioxa-1,11-undecylene, and $C_1$ to $C_{20}$ alkyl is for example methyl, ethyl, propyl, isopropyl, n-butyl, sec-butyl, tert-butyl, n-hexyl, n-heptyl, n-octyl, n-decyl, n-dodecyl, n-tetradecyl, n-hexadecyl, n-octadecyl, n-eicosyl or 2-ethylhexyl.

Preferably $R^1$, $R^2$ and $R^3$ each independently of one another are 1,2-ethylene, 1,2-propylene, 1,3-propylene, 1,4-butylene, 1,6-hexylene, 2,2-dimethyl-1,3-propylene, 3-oxa-1,5-pentylene, 3,6-dioxa-1,8-octylene or 3,6,9-trioxa-1,1'-undecylene, more preferably 1,2-ethylene, 1,2-propylene, 1,3-propylene, 1,4-butylene, 1,6-hexylene or 3-oxa-1,5-pentylene, very preferably 1,2-ethylene, 1,2-propylene, 1,4-butylene or 1,6-hexylene and especially 1,2-ethylene.

Preferably R is hydrogen or $C_1$-$C_4$ alkyl, i.e., methyl, ethyl, propyl, isopropyl, n-butyl, sec-butyl or tert-butyl, more preferably hydrogen, methyl or n-butyl, very preferably hydrogen or methyl, and especially hydrogen.

Examples of compounds containing a hydroxyl or amino group and at least one vinyl, methacryloyl or acryloyl group are those containing precisely one hydroxyl or amino group, preferably a hydroxyl group, and at least one, 1 to 10 for example, preferably 1 to 6, more preferably 1 to 4, very preferably 1 to 3, in particular 1 or 2 and especially one vinyl, methacryloyl or acryloyl group.

These may be, for example, vinyl ethers or (meth)acrylic esters of polyetherols, polyesterols, urethane alcohols, carbonate alcohols, or epoxy alcohols, preferably polyether (meth)acrylates, polyesterol (meth)acrylates, urethane (meth)acrylates or epoxy (meth)acrylates.

Preferred compounds are those as described in EP-A1 54 105, p. 2 line 13 to p. 5 line 36, and in the examples there; in EP-A2 279 303, p. 2 line 36 to p. 3 line 34 and in the examples there; in EP-A1 686 621, p. 2 line 42 to p. 4 line 47 and in the examples there; in EP-A1 921 168, column 1 line 57 to column 6 line 20 and in the examples there; and in DE-A1 33 16 593, p. 5 line 14 to p. 10 line 4 and in the examples there. These five cited publications are hereby expressly part of the present disclosure content.

Particularly preferred compounds containing a hydroxyl or amino group and at least one vinyl, methacryloyl or acryloyl group are alcohols or amines of the formula (VII)

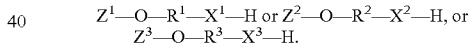

In these formulae
$X^1$, $X^2$ and $X^3$ each independently of one another are preferably oxygen and
$Z^1$, $Z^2$ and $Z^3$ are each independently of one another preferably methacryloyl (—(CO)—C(CH₃)=CH₂) or acryloyl (—(CO)—C(H)=CH₂), more preferably acryloyl.

Preferred compounds of formula (VII) are 2-hydroxyethyl (meth)acrylate, 2-hydroxypropyl (meth)acrylate, 4-hydroxybutyl (meth)acrylate, 6-hydroxyhexyl (meth)acrylate, diethylene glycol mono(meth)acrylate, dipropylene glycol mono(meth)acrylate or 4-hydroxybutyl vinyl ether. Further suitable compounds include trimethylolpropane diacrylate and pentaerythrityl diacrylate and triacrylate. Particular preference is given to 2-hydroxyethyl (meth)acrylate, 2-hydroxypropyl (meth)acrylate, 4-hydroxybutyl (meth)acrylate, 6-hydroxyhexyl (meth)acrylate, pentaerythrityl triacrylate and diethylene glycol mono(meth)acrylate, and very particular preference is given to 2-hydroxyethyl (meth)acrylate and 2-hydroxypropyl (meth)acrylate, in particular 2-hydroxyethyl (meth)acrylate and especially 2-hydroxyethyl acrylate.

Compound (I) can be used with advantage as a crosslinker in radiation-curable coating materials.

Compounds (II) and (V) can be used as crosslinkers in radiation-curable coating materials and additionally can also be crosslinked, for example, thermally with amino- or hydroxy-containing compounds.

Compounds (III) and (VI) can be used as crosslinkers in thermally curable coating materials together with amino- or hydroxy-containing compounds and additionally can be radiation-cured.

As a result of the absence of halogen atoms the compounds of the invention do not exhibit the yellowing tendency and UV sensitivity known from the prior art.

As a result of their high functionality density the compounds are able to achieve a high degree of crosslinking of coatings.

Because of their functional groups that can be cured via different curing mechanisms, the compounds (II), (III), (V) and (VI) in particular can be used with advantage in dual-cure coating materials. The coatings comprising compounds of the invention may after curing exhibit improved hardness and/or scratch resistance.

The terms "dual cure" and "multicure" refer in the context of this publication to a curing operation which takes place via two or more than two, respectively, mechanisms, selected for example from radiation, moisture, chemical, oxidative and/or thermal curing, preferably selected from radiation, moisture, chemical and/or thermal curing, more preferably selected from radiation, chemical and/or thermal curing, and very preferably from radiation-curing and chemical curing.

By chemical curing is meant an operation which takes place by a chemical reaction in the coating material: for example, by reaction of epoxide groups with amines or, preferably, isocyanate groups with alcohols or amines or by reaction of carbamyl groups with alcohols.

Compounds (I), (II) and (III) can be prepared by purely thermal reaction or, preferably, by a catalyzed reaction of compounds of formula (IV) with compounds of formula (VII).

In the case of a thermal reaction regime the reaction is conducted at a temperature up to 140° C., preferably up to 130° C.

Since the temperature in the catalyzed process is lower than in the case of purely thermal preparation, more favorable color numbers are achievable.

The radicals $R^4$-$R^6$ are derived each independently of one another from alcohols $R^4OH$, $R^5OH$ and $R^6OH$ which have an atmospheric pressure boiling point of 120° C. or less, preferably of 100° C. or less, more preferably of 80° C. or less and very preferably of 70° C. or less.

Examples of the radicals $R^4$, $R^5$ and $R^6$ each independently of one another are methyl, ethyl, iso-propyl, n-propyl, n-butyl, iso-butyl, sec-butyl or tert-butyl, preferably methyl, ethyl or n-butyl, very preferably methyl or n-butyl, and especially methyl.

The radicals $R^4$, $R^5$ and $R^6$ can be identical or different, but preferably not more than two different radicals are involved.

1,3,5-Triazine carbamates (IV) used with preference are the methyl-1,3,5-triazine carbamates, ethyl-1,3,5-triazine carbamates, n-butyl-1,3,5-triazine carbamates or mixed methyl/n-butyl-1,3,5-triazine carbamates.

Particular preference in the process of the invention is given to those alcohols and/or amines (VII) of which the lowest-boiling one has a boiling-point difference of at least 20° C., preferably at least 40° C. and more preferably at least 60° C. from the highest-boiling of the alcohols $R^4OH$, $R^5OH$ and $R^6OH$.

In the case of the catalyzed reaction regime the catalyst in accordance with the invention is preferably selected from the group comprising tin compounds, cesium salts, alkali metal carbonates and tertiary amines.

Tin compounds are all organometallic tin compounds, preferably tin(II) n-octanoate, tin(II) 2-ethylhexanoate, tin (II) laurate, dibutyltin oxide, dibutyltin dichloride, dibutyltin diacetate, dibutyltin dilaurate, dibutyltin dimaleate or dioctyltin diacetate, more preferably tin(II) n-octanoate, tin(II) 2-ethylhexanoate, tin(II) laurate, dibutyltin oxide, dibutyltin diacetate or dibutyltin dilaurate, very preferably dibutyltin oxide, dibutyltin diacetate or dibutyltin dilaurate and especially dibutyltin dilaurate.

Tin compounds, however, are toxicologically objectionable and are therefore less preferred in accordance with the invention, particularly when they remain in the reaction mixture. Contrastingly cesium salts and alkali metal carbonates are unobjectionable.

Preferred cesium salts are those comprising the following anions: $F^-$, $Cl^-$, $ClO^-$, $ClO_3^-$, $ClO_4^-$, $Br^-$, $I^-$, $IO_3^-$, $CN^-$, $OCN^-$, $NO_2^-$, $NO_3^-$, $HCO_3^-$, $CO_3^{2-}$, $S^{2-}$, $SH^-$, $HSO_3^-$, $SO_3^{2-}$, $HSO_4^-$, $SO_4^{2-}$, $S_2O_2^{2-}$, $S_2O_4^{2-}$, $S_2O_5^{2-}$, $S_2O_6^{2-}$, $S_2O_7^{2-}$, $S_2O_8^{2-}$, $H_2PO_2^-$, $H_2PO_4^-$, $HPO_4^{2-}$, $PO_4^{3-}$, $P_2O_7^{4-}$, $(OC_mH_{2m+1})^-$, $(C_mH_{2m-1}O_2)^-$, $(C_mH_{2m-3}O_2)^-$ and $(C_{m+1}H_{2m-2}O_4)^{2-}$, m standing for the numbers 1 to 20.

Particular preference is given to cesium carboxylates where the anion conforms to formulae $(C_mH_{2m-1}O_2)^-$ and $(C_{m+1}H_{2m-2}O_4)^{2-}$ with m being 1 to 20. Especially preferred cesium salts have monocarboxylate anions of general formula $(C_mH_{2m-1}O_2)^-$, m being from 1 to 20. Particular mention may be made in this context of formate, acetate, propionate, hexanoate and 2-ethylhexanoate, with very particular preference being given to cesium acetate.

The cesium salts can be added to the batch in solid form or in dissolved form. Suitable solvents are polar aprotic solvents or else protic solvents. Particularly suitable solvents besides water are alcohols; very particular suitability is possessed by polyols, such as ethanediols, propanediols or butanediols, and glycol ethers, for example.

In order to improve the solubility of the cesium salts in the reaction medium they can be used if appropriate with phase transfer catalysts. Suitable phase transfer catalysts are, for example, crown ethers such as 18-crown-6 or tetraalkylammonium salts such as tetrabutylammonium bromide.

Alkali metal carbonates are for example $Li_2CO_3$, $Na_2CO_3$ and $K_2CO_3$ and also the hydrogen carbonates $LiHCO_3$, $NaHCO_3$ and $KHCO_3$, preference being given to $Na_2CO_3$ and $K_2CO_3$ and particular preference to $K_2CO_3$.

Tertiary amines are for example trioctylamine, tridodecylamine, tribenzylamine, N,N,N',N'-tetramethylethylenediamine, 1-methylpyrrole, pyridine, 4-dimethylaminopyridine, picoline, N,N'-dimethylpiperazine, N-methylmorpholine, N-methylpiperidine, N-ethylpiperidine, N,N-dimethylaniline, N,N-dimethylbenzylamine, N-methylimidazole, 1,4-diazabicyclo[2.2.2]octane, 1,5-diazabicyclo[4.3.0]non-5-ene or 1,8-diazabicyclo[5.4.0]undec-7-ene.

Preferred catalysts are cesium salts and alkali metal carbonates, particular preference being given to the cesium salts.

Catalysts that might further be contemplated include alkoxides (examples being sodium or potassium alkoxides of $C_1$-$C_4$ alkyl alcohols, preferably sodium and potassium methoxide and ethoxide), hydroxides (NaOH, KOH, Ca(OH)$_2$, for example), carboxylates (examples being sodium or potassium salts of $C_1$-$C_4$ alkylcarboxylic acids or $ClCH_2COONa$), oxides (CaO, MgO, ZnO, $Tl_2O_3$, PbO, for example), phosphines ($PPh_3$ for example), zinc salts ($ZnCl_2$) and ion exchangers (strongly or weakly alkaline anion exchangers, such as DOWEX® MSA-1).

The catalyst is used usually in amounts from 0.001 to 0.3 mol %, preferably 0.005 to 0.25 mol %, more preferably 0.01 to 0.2 mol % and very preferably 0.02 to 0.1 mol %, based on the starting compound (II).

The reaction is carried out in accordance with the invention at a temperature of at least 40° C., preferably at least 50° C., more preferably at least 60° C. and very preferably at least 70° C.

The reaction temperature is preferably above the boiling temperature of the alcohol $R^4OH$, $R^5OH$ or $R^6OH$ that is to be separated off.

In accordance with the invention the upper temperature limit is generally not more than 120° C., in particular not more than 110° C.

In order to reduce polymerization of the compounds (VII) containing double bonds the reaction is conducted preferably in the presence of free-radical stabilizers. Examples of suitable free-radical stabilizers include 4-methoxyphenol (100-4000 ppm), 2,6-di-t-butylhydroquinone (50-1000 ppm), phenothiazine (10-500 ppm), triphenyl phosphite (50-1000 ppm) and 4-hydroxy-2,2,6,6-tetramethylpiperidine-N-oxyl (10-500 ppm).

An advantage of the catalyzed reaction is that by adding the catalyst with the same or a shorter reaction time and at least equal conversions under otherwise identical conditions the reaction temperature can be lowered by at least 10° C., preferably at least 15° C. and more preferably at least 20° C. as compared with the uncatalyzed reaction.

The reaction time varies according to substrate and can be from 15 minutes to 12 hours, preferably 30 minutes to 10 hours, more preferably 45 minutes to 8 hours and very preferably 1 to 7 hours.

The stoichiometry with respect to alcohol and/or amine (VII) employed in relation to carbamate groups to be converted in (IV) is generally 0.5-1.5:1 mol/mol, preferably 0.7-1.3:1, more preferably 0.8-1.2:1, very preferably 0.8-1.1:1, in particular 0.9-1:1, and especially 0.95-1.0:1 mol/mol.

Depending on the chosen stoichiometry between (IV) and (VII) the fractions of (I), (II) and (III) in the reaction mixture vary.

If an excess of compound (VII) is used it can preferably remain in the reaction mixture and in the coating material before then being incorporated into the binder in the course of curing via a free-radical or chemical curing mechanism.

The reaction can take place in bulk or in a suitable solvent, i.e., a solvent that does not react with a 1,3,5-triazine carbamate or 1,3,5-triazine urea. Examples of possible such solvents include acetone, acetylacetone, acetoacetic esters, ethyl acetate, butyl acetate, ethylene glycol dimethyl ether, ethylene glycol diethyl ether, ethylene glycol di-n-butyl ether, diethylene glycol dimethyl ether, diethylene glycol diethyl ether, diethylene glycol di-n-butyl ether, $C_1$-$C_4$ alkylene carbonates, especially propylene carbonate, THF, dioxane, dimethylformamide, dimethyl sulfoxide, N-methylpyrrolidone, 1,3-dioxolane, iso-butyl methyl ketone, ethyl methyl ketone, diethyl ether, tert-butyl methyl ether, tert-butyl ethyl ether, n-pentane, n-hexane, n-heptane, cyclohexane, methylcyclohexane, benzene, toluene, xylene, paraffins, naphtha, mineral oil or petroleum ether fractions.

Preferably the reaction is conducted in bulk.

The conversion rates achieved with the process specified are generally at least 20%, preferably at least 30%, more preferably at least 40% and very preferably at least 60%.

The reaction can be conducted in a gas or gas mixture which is inert under the reaction conditions, examples being gas mixtures with an oxygen content below 10%, preferably below 8% and more preferably below 7% by volume, preference being given to nitrogen, argon, helium, nitrogen/noble gas mixtures, carbon dioxide or carbon monoxide, and particular preference to nitrogen.

In one preferred embodiment of the process of the invention the liberated lower alcohols $R^4OH$, $R^5OH$ and $R^6OH$ are separated off appropriately so as to shift the reaction equilibrium in favor of the product.

The lower alcohol $R^4OH$, $R^5OH$ or $R^6OH$ can be separated off for example by distillation, stripping, vacuum, azeotropic removal, absorption, pervaporation and diffusion via membranes.

Preference is given to distillative removal, if appropriate under reduced pressure (vacuum), which if appropriate can be assisted by stripping with a gas which is inert under the reaction conditions.

For stripping, a gas mixture or gas which is inert under the reaction conditions is passed through the reaction mixture, by being bubbled in, for example.

Absorption can take place for example with molecular sieves (pore size in the region, for example, of about 3-10 angstroms). Diffusion can take place, for example, by means of suitable semipermeable membranes.

The reaction can take place in accordance with the invention continuously, batchwise or semibatchwise, preferably batchwise or semibatchwise.

For that purpose in general the starting material of formula (IV) is introduced as an initial charge and brought to the desired reaction temperature.

Before or after the desired reaction temperature has been reached, the catalyst can be added at least in part and the alcohol/amine (VII) can be added in full, in portions or continuously. If the catalyst has not yet been added in full it too may be added subsequently in portions.

It can be advantageous to raise the reaction temperature in the course of the reaction, by at least 10° C. for example, preferably by at least 15° C. and more preferably by at least 20° C. in relation to the temperature at the start of the reaction.

The course of the reaction can be monitored, for example, by monitoring the amount of liberated alcohol $R^4OH$, $R^5OH$ or $R^6OH$ and terminating the reaction when the desired conversion rate has been achieved.

The reaction can be stopped, for example, by cooling down or by direct cooling with a solvent.

The reaction is preferably carried out in a backmixed reaction tank in which mixing can be accomplished for example by stirring, introduction through nozzles or a pumped circulation.

The temperature adjustment can either be via the reactor walls or by means of a heat exchanger in the pumped circulation.

If the liberated lower alcohol $R^4OH$, $R^5OH$ or $R^6OH$ is separated off by distillation and/or stripping, then the reactor may be surmounted by a packed column or tray column, for which 2 to 10 theoretical plates are generally sufficient.

Separation of the lower alcohol can be assisted by applying a slight vacuum: for example, the reaction can be carried out at a pressure of from 200 hPa to atmospheric pressure, preferably 300 hPa to atmospheric pressure, more preferably 500 hPa to atmospheric pressure, very preferably at 800 hPa to atmospheric pressure, and in particular at atmospheric pressure.

After the end of the reaction the reaction mixture may additionally be subjected to washing and/or decoloring.

For washing, the reaction mixture is treated in a washer with a washing fluid, an example being water or a 5-30%, preferably 5-20%, more preferably 5-15% strength by weight solution of sodium chloride, potassium chloride, ammonium chloride, sodium sulfate or ammonium sulfate, preferably water or sodium chloride solution.

Washing can be carried out, for example, in a stirred vessel or in other conventional apparatus, e.g., in a column or mixer-settler apparatus.

The reaction mixture can if necessary be subjected to decoloring, by treatment for example with activated carbon or metal oxides, such as alumina, silicon oxide, magnesium oxide, zirconium oxide, boron oxide or mixtures thereof, in amounts for example of 0.1-50% by weight, preferably 0.5 to 25% by weight, more preferably 1-10% by weight, and at temperatures of for example 10 to 100° C., preferably 20 to 80° C. and more preferably 30 to 60° C.

This can take place by adding the pulverulent or granular decolorant to the reaction mixture with subsequent filtration, or by passing the reaction mixture over a bed of the decolorant in the form of any desired suitable shaped bodies.

In general the composition of the reaction mixture obtainable under the stated reaction conditions is as follows:
(I) 5-80% by weight,
(II) 10-60% by weight,
(III) 10-40% by weight,
(IV) 0-20% by weight,
(VII) 0-10% by weight,
with the proviso that the sum thereof is 100% by weight,
and also, if appropriate, 2-amino-4,6-biscarbamoyl-1,3,5-triazine or 2,4-diamino-6-carbamoyl-1,3,5-triazine as reaction by-products in fractions below 10 percent by weight. By-products of this kind may come about by example through hydrolysis of compounds of formulae (I) to (VI), such as during the reaction according to the invention, or as a result of water present in the coating material.

Accordingly compounds of formula (IX)

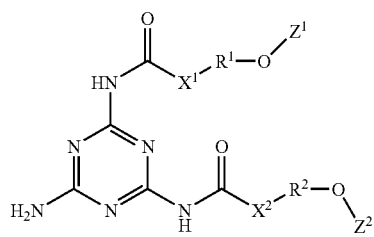

and (X)

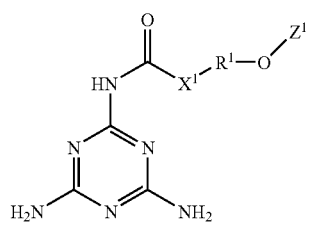

in which
$R^1$, $R^2$, $X^1$, $X^2$, $Z^1$ and $Z^2$ are as defined above,
are further provided by the present invention.

Compounds of formula (IX) and (X) are likewise free-radically copolymerizable and in the case of compound (IX) have a crosslinking action.

The preparation of compounds (I), (V) and (VI) from 2,4,6-triisocyanato-1,3,5-triazine may in principle take place in the same way as described above from the compound (IV), but with the following differences:

The stoichiometry in respect of alcohol or amine (VII) used in relation to isocyanate groups to be converted in 2,4,6-triisocyanato-1,3,5-triazine is generally 0.5-1.2:1 mol/mol, preferably 0.7-1.1:1, more preferably 0.8-1.1:1, very preferably 0.9-1.1:1, in particular 0.9-1:1 and especially 0.95-1.0:1 mol/mol.

In general the reaction is carried out at temperatures between 5 and 100° C., preferably between 20 to 90° C. and more preferably between 40 and 80° C., and in particular between 60 and 80° C.

It is preferred to operate under anhydrous conditions.

Anhydrous here means that the water content of the reaction system is not more than 5% by weight, preferably not more than 3% by weight and more preferably not more than 1% by weight.

The reaction of the diisocyanates can be accelerated using the customary catalysts. Suitable for this purpose in principle are all of the catalysts normally used in polyurethane chemistry.

These catalysts are, for example, organic amines, especially tertiary aliphatic, cycloaliphatic or aromatic amines, and/or Lewis-acidic organometallic compounds. Examples of suitable Lewis-acidic organometallic compounds include the abovementioned tin compounds, such as tin(II) salts of organic carboxlic acids, e.g., tin(II) acetate, tin(II) octoate, tin(II) ethylhexoate and tin(II) laurate, and the dialkyltin(IV) salts of organic carboxylic acids, e.g., dimethyltin diacetate, dibutyltin diacetate, dibutyltin dibutyrate, dibutyltin bis(2-ethylhexanoate), dibutyltin dilaurate, dibutyltin maleate, dioctyltin dilaurate and dioctyltin diacetate. Metal complexes such as acetylacetonates of iron, titanium, aluminum, zirconium, manganese, nickel and cobalt are also possible. Further metal catalysts are described by Blank et al. in Progress in Organic Coatings, 1999, vol. 35, pages 19-29.

Preferred Lewis-acidic organic organometallic compounds are dimethyltin diacetate, dibutyltin dibutyrate, dibutyltin bis(2-ethylhexanoate), dibutyltin dilaurate, dioctyltin dilaurate, zirconium acetylacetonate and zirconium 2,2,6,6-tetramethyl-3,5-heptanedionate.

Bismuth catalysts and cobalt catalysts as well, and also cesium salts, can be used as catalysts. Suitable cesium salts include the compounds mentioned above, preferably cesium acetate.

Washing is generally omitted, owing to the reactivity of the isocyanate groups in the compounds (V) and (VI).

The 1,3,5-triazine carbamates and ureas of the invention, of formulae (I), (II), (III), (V) and (VI), can be used for coating a variety of substrates, such as wood, wood veneer, paper, paperboard, cardboard, textile, leather, nonwoven, plastics surfaces, glass, ceramic, mineral building materials, and uncoated or coated metals.

Where they are used in coating compositions, the 1,3,5-triazine carbamates and ureas of the invention can be employed in particular in primers, surfacers, pigmented topcoat and clearcoat materials in the sector of automotive refinish or large-vehicle finishing. Coating compositions of this kind are particularly suitable for applications which call for particularly high application reliability, exterior weathering stability, optical qualities, solvent resistance, chemical resistance and water resistance, such as in automotive refinish and large-vehicle finishing.

The present invention further provides radiation-curable coating materials comprising
at least one compound of the formula (I), (II), (III), (V) or (VI),
if appropriate a compound having one or more than one free-radically polymerizable double bond, if appropriate at least one photoinitiator, and
if appropriate further, typical coatings additives.

Compounds (I), (II), (III), (V) or (VI) of the invention can be used as sole binder or in combination with a further free-radically polymerizable compound.

Compounds having one or more than one free-radically polymerizable double bond are for example those compounds which contain 1 to 6, preferably 1 to 4 and more preferably 1 to 3 free-radically polymerizable groups.

Free-radically polymerizable groups are for example vinyl ether or (meth)acrylate groups, preferably (meth)acrylate groups and more preferably acrylate groups.

Free-radically polymerizable compounds are often divided into monofunctional (compound with one free-radically polymerizable double bond) and polyfunctional (compound with more than one free-radically polymerizable double bond) polymerizable compounds.

Monofunctional polymerizable compounds are those having exactly one free-radically polymerizable group, polyfunctional polymerizable compounds being those having more than one—preferably at least two—free-radically polymerizable group(s).

Monofunctional polymerizable compounds are for example esters of (meth)acrylic acid with alcohols containing 1 to 20 carbon atoms, e.g., methyl (meth)acrylate, ethyl (meth)acrylate, butyl (meth)acrylate, 2-ethylhexyl (meth)acrylate, 2-hydroxyethyl (meth)acrylate, 2-hydroxypropyl (meth)acrylate, 4-hydroxybutyl (meth)acrylate, dihydrodicyclopentadienyl acrylate, vinylaromatic compounds, e.g., styrene, divinylbenzene, α,β-unsaturated nitriles, such as acrylonitrile, methacrylonitrile, α,β-unsaturated aldehydes, e.g., acrolein, methacrolein, vinyl esters, e.g., vinyl acetate, vinyl propionate, halogenated ethylenically unsaturated compounds, e.g., vinyl chloride, vinylidene chloride, conjugated unsaturated compounds, e.g., butadiene, isoprene, chloroprene, monounsaturated compounds, e.g., ethylene, propylene, 1-butene, 2-butene, isobutene, cyclic monounsaturated compounds, e.g., cyclopentene, cyclohexene, cyclododecene, N-vinylformamide, allylacetic acid, vinylacetic acid, monoethylenically unsaturated carboxylic acids having 3 to 8 carbon atoms and their water-soluble alkali metal, alkaline earth metal or ammonium salts such as for example: acrylic acid, methacrylic acid, dimethylacrylic acid, ethacrylic acid, maleic acid, citraconic acid, methylenemalonic acid, crotonic acid, fumaric acid, mesaconic acid and itaconic acid, maleic acid, N-vinylpyrrolidone, N-vinyllactams, such as N-vinylcaprolactam, N-vinyl-N-alkylcarboxamides or N-vinylcarboxamides, such as N-vinylacetamide, N-vinyl-N-methylformamide and N-vinyl-N-methylacetamide, or vinyl ethers, e.g., methyl vinyl ether, ethyl vinyl ether, n-propyl vinyl ether, iso-propyl vinyl ether, n-butyl vinyl ether, sec-butyl vinyl ether, iso-butyl vinyl ether, tert-butyl vinyl ether, 4-hydroxybutyl vinyl ether, and mixtures thereof.

Preference among these is given to the esters of (meth)acrylic acid, particular preference is given to methyl (meth)acrylate, ethyl (meth)acrylate, n-butyl (meth)acrylate, 2-ethylhexyl (meth)acrylate and 2-hydroxyethyl acrylate, very particular preference to n-butyl (meth)acrylate, 2-ethylhexyl (meth)acrylate and 2-hydroxyethyl acrylate, and special preference to 2-hydroxyethyl acrylate.

(Meth)acrylic acid in this specification stands for methacrylic acid and acrylic acid, preferably for acrylic acid.

Polyfunctional polymerizable compounds are preferably polyfunctional (meth)acrylates which carry more than one, preferably 2-10, more preferably 2-6, very preferably 24 and in particular 2-3 (meth)acrylate groups, preferably acrylate groups.

These may be for example, esters of (meth)acrylic acid with polyalcohols which correspondingly are at least difunctional.

Suitable polyalcohols of this kind are, for example, at least difunctional polyols, polyetherols or polyesterols or polyacrylate polyols having an average OH functionality of at least 2, preferably 3 to 10.

Examples of polyfunctional polymerizable compounds are ethylene glycol diacrylate, 1,2-propanediol diacrylate, 1,3-propanediol diacrylate, 1,4-butanediol diacrylate, 1,3-butanediol diacrylate, 1,5-pentanediol diacrylate, 1,6-hexanediol diacrylate, 1,8-octanediol diacrylate, neopentyl glycol diacrylate, 1,1-, 1,2-, 1,3- and 1,4-cyclohexanedimethanol diacrylate, 1,2-, 1,3- or 1,4-cyclohexanediol diacrylate, trimethylolpropane triacrylate, ditrimethylolpropane pentaacrylate or hexaacrylate, pentaerythrityl triacrylate or tetraacrylate, glyceryl diacrylate or triacrylate, and also diacrylates and polyacrylates of sugar alcohols such as, for example, sorbitol, mannitol, diglycerol, threitol, erythritol, adonitol (ribitol), arabitol (lyxitol), xylitol, dulcitol (galactitol), maltitol or isomaltol, or of polyester polyols, polyetherols, polyTHF having a molar mass between 162 and 2000, poly-1,3-propanediol having a molar mass between 134 and 1178, polyethylene glycol having a molar mass between 106 and 898, and also epoxy (meth)acrylates, urethane (meth)acrylates or polycarbonate (meth)acrylates.

Further examples are (meth)acrylates of compounds of formulae (VIIIa) to (VIIIc),

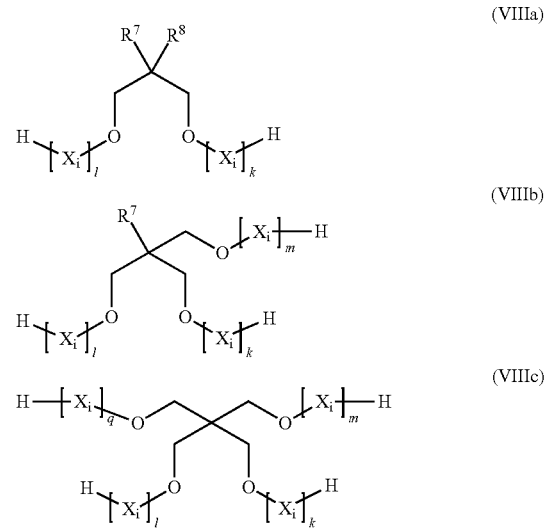

in which
$R^7$ and $R^8$ independently of one another are hydrogen or optionally aryl-, alkyl-, aryloxy-, alkyloxy-, heteroatom- and/or heterocycle-substituted $C_1$-$C_{18}$ alkyl,
k, l, m and q independently of one another are each an integer from 1 to 10, preferably from 1 to 5 and more preferably from 1 to 3, and
each $X_i$ for i=1 to k, 1 to l, 1 to m and 1 to q can be selected independently of the others from the group consisting of
—$CH_2$—$CH_2$—O—, —$CH_2$—$CH(CH_3)$—O—, —$CH(CH_3)$—$CH_2$—O—, —$CH_2$—$C(CH_3)_2$—O—, —$C(CH_3)_2$—$CH_2$—O—, —$CH_2$—CHVin-O—, —CHVin-$CH_2$—

O—, —CH₂—CHPh-O— and —CHPh-CH₂—O—, preferably from the group consisting of —CH₂—CH₂—O—, —CH₂—CH(CH₃)—O— and —CH(CH₃)—CH₂—O—, and more preferably —CH₂—CH₂—O—, Ph being phenyl and Vin being vinyl.

In these definitions unsubstituted or aryl-, alkyl-, aryloxy-, alkyloxy-, heteroatom- and/or heterocycle-substituted $C_1$-$C_{18}$ alkyl is for example methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethylpropyl, 1,1-dimethylbutyl or 1,1,3,3-tetramethylbutyl, preferably methyl, ethyl or n-propyl, very preferably methyl or ethyl.

These compounds are preferably (meth)acrylates of singly to vigintuply and more preferably triply to decuply ethoxylated, propoxylated or mixedly ethoxylated and propoxylated, and in particular exclusively ethoxylated, neopentyl glycol, trimethylolpropane, trimethylolethane or pentaerythritol.

Preferred polyfunctional polymerizable compounds are ethylene glycol diacrylate, 1,2-propanediol diacrylate, 1,3-propanediol diacrylate, 1,4-butanediol diacrylate, 1,6-hexanediol diacrylate, trimethylolpropane triacrylate, pentaerythrityl tetraacrylate, polyester polyol acrylates, polyetherol acrylates and triacrylate of singly to vigintuply alkoxylated—with particular preference ethoxylated—trimethylolpropane.

Especially preferred polyfunctional polymerizable compounds are 1,4-butandiol diacrylate, 1,6-hexanediol diacrylate, trimethylolpropane triacrylate, pentaerythrityl tetraacrylate and triacrylate of singly to vigintuply ethoxylated trimethylolpropane.

Polyester polyols are known for example from Ullmanns Enzyklopädie der technischen Chemie, 4th edition, volume 19, pp. 62 to 65. Preference is given to using polyester polyols obtained by reacting dihydric alcohols with dibasic carboxylic acids. Instead of the free polycarboxylic acids it is also possible to use the corresponding polycarboxylic anhydrides or corresponding polycarboxylic esters of lower alcohols, or mixtures thereof, to prepare the polyester polyols. The polycarboxylic acids may be aliphatic, cycloaliphatic, araliphatic, aromatic or heterocyclic and may if appropriate be substituted, by halogen atoms for example, and/or unsaturated. Examples of such that may be mentioned include the following:

Oxalic acid, maleic acid, fumaric acid, succinic acid, glutaric acid, adipic acid, sebacic acid, dodecanedioic acid, o-phthalic acid, isophthalic acid, terephthalic acid, trimellitic acid, azelaic acid, 1,4-cyclohexanedicarboxylic acid or tetrahydrophthalic acid, suberic acid, phthalic anhydride, tetrahydrophthalic anhydride, hexahydrophthalic anhydride, tetrachlorphthalic anhydride, endomethylenetetrahydrophthalic anhydride, glutaric anhydride, maleic anhydride, dimeric fatty acids, their isomers and hydrogenation products and also esterifiable derivatives, such as anhydrides or dialkyl esters, $C_1$-$C_4$ alkyl esters for example, preferably methyl, ethyl or n-butyl esters, of said acids. Preference is given to dicarboxylic acids of general formula HOOC—(CH₂)$_y$—COOH where y is a number from 1 to 20, preferably an even number from 2 to 20, more preferably succinic acid, adipic acid, sebacic acid and dodecanedicarboxylic acid.

Polyhydric alcohols suitable for preparing the polyesterols include 1,2-propanediol, ethylene glycol, 2,2-dimethyl-1,2-ethanediol, 1,3-propanediol, 1,2-butanediol, 1,3-butanediol, 1,4-butanediol, 3-methylpentane-1,5-diol, 2-ethylhexane-1, 3-diol, 2,4-diethyloctane-1,3-diol, 1,6-hexanediol, polyTHF with a molar mass between 162 and 2000, poly-1,3-propanediol with a molar mass between 134 and 1178, poly-1, 2-propanediol with a molar mass between 134 and 898, polyethylene glycol with a molar mass between 106 and 458, neopentyl glycol, neopentyl glycol hydroxypivalate, 2-ethyl-1,3-propanediol, 2-methyl-1,3-propanediol, 2,2-bis(4-hydroxycyclohexyl)-propane, 1,1-, 1,2-, 1,3- and 1,4-cyclohexanedimethanol, 1,2-, 1,3- or 1,4-cyclo-hexanediol, trimethylolbutane, trimethylolpropane, trimethylolethane, pentaerythritol, glycerol, ditrimethylolpropane, dipentaerythritol, sorbitol, mannitol, diglycerol, threitol, erythritol, adonitol (ribitol), arabitol (Iyxitol), xylitol, dulcitol (galactitol), maltitol or isomalt, which if appropriate may have been alkoxylated as described above.

Preferred alcohols are those of general formula HO—(CH₂)$_x$—OH where x is a number from 1 to 20, preferably an even number from 2 to 20. Preference is given to ethylene glycol, butane-1,4-diol, hexane-1,6-diol, octane-1,8-diol and dodecane-1,12-diol. Preference is further given to neopentyl glycol.

Also suitable are polycarbonate diols, such as may be obtained, for example, by reacting phosgene with an excess of the low molecular mass alcohols specified as synthesis components for the polyester polyols.

Also suitable are lactone-based polyester diols, which are homopolymers or copolymers of lactones, preferably hydroxy-terminal adducts of latones with suitable difunctional starter molecules. Suitable lactones are preferably those derived from compounds of general formula HO—(CH₂)$_z$—COOH, where z is a number from 1 to 20 and one hydrogen atom of a methylene unit may also be substituted by a $C_1$ to $C_4$ alkyl radical. Examples are ε-caprolactone, β-propiolactone, gamma-butyrolactone and/or methyl-ε-caprolactone, 4-hydroxybenzoic acid, 6-hydroxy-2-naphthoic acid or pivalolactone and also mixtures thereof. Suitable starter components are, for example, the low molecular mass dihydric alcohols specified above as a synthesis component for the polyester polyols. The corresponding polymers of ε-caprolactone are particularly preferred. Lower polyester diols or polyether diols as well can be used as starters for preparing the lactone polymers. Instead of the polymers of lactones it is also possible to use the corresponding, chemically equivalent polycondensates of the hydroxycarboxylic acids corresponding to the lactones. The polyfunctional polymerizable compound may further comprise urethane (meth)acrylates, epoxy (meth)acrylates or carbonate (meth)acrylates.

Urethane (meth)acrylates, for example, are obtainable by reacting polyisocyanates with hydroxyalkyl (meth)acrylates or hydroxyalkyl vinyl ethers and if appropriate chain extenders such as diols, polyols, diamines, polyamines or dithiols or polythiols. Urethane (meth)acrylates which can be dispersed in water without adding emulsifiers further comprise ionic and/or nonionic hydrophilic groups, which are introduced into the urethane by means for example of synthesis components such as hydroxycarboxylic acids.

The polyurethanes which can be used comprise as synthesis components essentially:

(a) at least one organic aliphatic, aromatic or cycloaliphatic di- or polyisocyanate,
(b) at least one compound having at least one isocyanate-reactive group and at least one free-radically polymerizable unsaturated group, and
(c) if appropriate at least one compound having at least two isocyanate-reactive groups.

Examples of suitable components (a) include aliphatic, aromatic, and cycloaliphatic diisocyanates and polyisocyanates having an NCO functionality of at least 1.8, preferably from 1.8 to 5, and more preferably from 2 to 4, and also their isocyanurates, biurets, allophanates, and uretdiones.

The diisocyanates are preferably isocyanates having 4 to 20 carbon atoms. Examples of suitable diisocyanates are aliphatic diisocyanates such as tetramethylene diisocyanate, hexamethylene diisocyanate (1,6-diisocyanatohexane), octamethylene diisocyanate, decamethylene diisocyanate, dodecamethylene diisocyanate, tetradecamethylene diisocyanate, derivatives of lysine diisocyanate, tetramethyl-xylylene diisocyanate, trimethylhexane diisocyanate or tetramethylhexane diisocyanate, cycloaliphatic diisocyanates such as 1,4-, 1,3- or 1,2-diisocyanatocyclo-hexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis(iso-cyanatomethyl)cyclohexane or 2,4- or 2,6-diisocyanato-1-methylcyclohexane, and aromatic diisocyanates such as 2,4- or 2,6-tolylene diisocyanate and the isomer mixtures thereof, m- or p-xylylene diisocyanate, 2,4'- or 4,4'-diisocyanatodiphenyl-methane and the isomer mixtures thereof, 1,3- or 1,4-phenylene diisocyanate, 1-chloro-2,4-phenylene diisocyanate, 1,5-naphthylene diisocyanate, diphenylene 4,4'-diisocyanate, 4,4'-diisocyanato-3,3'-dimethylbiphenyl, 3-methyldiphenylmethane 4,4'-diisocyanate, tetramethylxylylene diisocyanate, 1,4-diisocyanatobenzene or diphenyl ether 4,4'-diisocyanate.

Mixtures of said diisocyanates may also be present.

Preference is given to hexamethylene diisocyanate, 1,3-bis(isocyanatomethyl)cyclo-hexane, isophorone diisocyanate and di(isocyanatocyclohexyl)methane.

Suitable polyisocyanates include polyisocyanates containing isocyanurate groups, uretdione diisocyanates, polyisocyanates containing biuret groups, polyisocyanates containing urethane groups or allophanate groups, polyisocyanates comprising oxadiazinetrione groups, uretonimine-modified polyisocyanates of linear or branched $C_4$-$C_{20}$ alkylene diisocyanates, cycloaliphatic diisocyanates having 6 to 20 carbon atoms in all or aromatic diisocyanates having 8 to 20 carbon atoms in all, or mixtures thereof.

The diisocyanates and polyisocyanates which can be used preferably have an isocyanate group (calculated as NCO, molecular weight=42) content of from 10 to 60% by weight based on the diisocyanate and polyisocyanate (mixture), more preferably from 15 to 60% by weight, and very preferably from 20 to 55% by weight. Preference is given to aliphatic and/or cycloaliphatic diisocyanates and polyisocyanates, examples being the abovementioned aliphatic and cycloaliphatic diisocyanates, respectively, or mixtures thereof.

Preference extends to
1) Polyisocyanates containing isocyanurate groups and formed from aromatic, aliphatic and/or cycloaliphatic diisocyanates. Particular preference is given here to the corresponding aliphatic and/or cycloaliphatic isocyanato-isocyanurates and, in particular, to those based on hexamethylene diisocyanate and isophorone diisocyanate. The isocyanurates present are, in particular, trisisocyanatoalkyl or trisisocyanatocycloalkyl isocyanurates, which represent cyclic trimers of the diisocyanates, or are mixtures with their higher homologs containing more than one isocyanurate ring. The isocyanato-isocyanurates generally have an NCO content of from 10 to 30% by weight, in particular from 15 to 25% by weight, and an average NCO functionality of from 3 to 4.5.
2) Uretdione diisocyanates having aromatically, aliphatically and/or cycloaliphatically attached isocyanate groups, preferably aliphatically and/or cycloaliphatically attached isocyanate groups, and especially those derived from hexamethylene diisocyanate or isophorone diisocyanate. Uretdione diisocyanates are cyclic dimerization products of diisocyanates.

In the formulations the uretdione diisocyanates can be used as sole component or in a mixture with other polyisocyanates, especially those specified under 1).
3) Polyisocyanates containing biuret groups and having aromatically, cycloaliphatically or aliphatically attached, preferably cycloaliphatically or aliphatically attached, isocyanate groups, especially tris(6-isocyanatohexyl)biuret or its mixtures with its higher homologs. These polyisocyanates containing biuret groups generally have an NCO content of from 18 to 22% by weight and an average NCO functionality of from 3 to 4.5.
4) Polyisocyanates containing urethane and/or allophanate groups and having aromatically, aliphatically or cycloaliphatically attached, preferably aliphatically or cycloaliphatically attached, isocyanate groups, as obtainable for example by reacting excess amounts of hexamethylene diisocyanate or of isophorone diisocyanate with polyhydric alcohols such as trimethylolpropane, neopentyl glycol, pentaerythritol, 1,4-butanediol, 1,6-hexanediol, 1,3-propanediol, ethylene glycol, diethylene glycol, glycerol, 1,2-dihydroxypropane or mixtures thereof. These polyisocyanates containing urethane and/or allophanate groups generally have an NCO content of from 12 to 20% by weight and an average NCO functionality of from 2.5 to 3.
5) Polyisocyanates comprising oxadiazinetrione groups, preferably derived from hexamethylene diisocyanate or isophorone diisocyanate. Polyisocyanates of this kind comprising oxadiazinetrione groups can be prepared from diisocyanate and carbon dioxide.
6) Uretonimine-modified polyisocyanates.

The polyisocyanates 1) to 6) can be used in a mixture, including if appropriate in a mixture with diisocyanates.

Suitable components (b) include compounds which carry at least one isocyanate-reactive group and at least one free-radically polymerizable group.

Possible examples of isocyanate-reactive groups include for example —OH, —SH, —$NH_2$ and —$NHR^9$, $R^9$ being hydrogen or an alkyl group comprising 1 to 4 carbon atoms, such as methyl, ethyl, n-propyl, iso-propyl, n-butyl, iso-butyl, sec-butyl or tert-butyl, for example.

Components (b) can be, for example, monoesters of $\alpha,\beta$-unsaturated carboxylic acids, such as acrylic acid, methacrylic acid, crotonic acid, itaconic acid, fumaric acid, maleic acid, acrylamidoglycolic acid, methacrylamidoglycolic acid or vinyl ethers with diols or polyols, having preferably 2 to 20 carbon atoms and at least two hydroxyl groups, such as ethylene glycol, diethylene glycol, triethylene glycol, 1,2-propylene glycol, 1,3-propylene glycol, 1,1-dimethyl-1,2-ethanediol, dipropylene glycol, triethylene glycol, tetraethylene glycol, pentaethylene glycol, tripropylene glycol, 1,4-butanediol, 1,5-pentanediol, neopentyl glycol, 1,6-hexanediol, 2-methyl-1,5-pentanediol, 2-ethyl-1,4-butanediol, 1,4-dimethylolcyclohexane, 2,2-bis(4-hydroxycyclohexyl)propane, glycerol, trimethylolethane, trimethylolpropane, trimethylolbutane, pentaerythritol, ditrimethylolpropane, erythritol, sorbitol, polyTHF with a molar weight between 162 and 2000, poly-1,3-propanediol with a molar weight between 134 and 400 or polyethylene glycol with a molar weight between 238 and 458. Additionally it is also possible to use esters or amides of (meth)acrylic acid with amino alcohols, e.g., 2-aminoethanol, 2-(methylamino)ethanol, 3-amino-1-propanol, 1-amino-2-propanol or 2-(2- aminoethoxy)ethanol, 2-mercaptoethanol or polyaminoalkanes, such as ethylenediamine or diethylenetriamine, or vinylacetic acid.

Also suitable in addition are unsaturated polyetherols or polyesterols or polyacrylate polyols having an average OH functionality of 2 to 10.

Examples of amides of ethylenically unsaturated carboxylic acids with amino alcohols are hydroxyalkyl(meth)acrylamides such as N-hydroxy-methylacryl-amide, N-hydroxymethylmethacrylamide, N-hydroxyethylacrylamide, N-hydroxyethylmethacrylamide, 5-hydroxy-3-oxapentyl (meth)acrylamide, N-hydroxyalkylcrotonamides such as N-hydroxymethylcrotonamide or N-hydroxyalkylmaleimides such as N-hydroxyethylmaleimide.

Preference is given to using 2-hydroxyethyl (meth)acrylate, 2- or 3-hydroxypropyl (meth)acrylate, 1,4-butanediol mono(meth)acrylate, neopentyl glycol mono(meth)acrylate, 1,5-pentanediol mono(meth)acrylate, 1,6-hexanediol mono (meth)acrylate, glyceryl mono(meth)acrylate and di(meth) acrylate, trimethylolpropane mono(meth)acrylate and di(meth)acrylate, pentaerythrityl mono(meth)acrylate, di(meth)acrylate and tri(meth)acrylate and also 4-hydroxybutyl vinyl ether, 2-aminoethyl (meth)acrylate, 2-aminopropyl (meth)acrylate, 3-aminopropyl (meth)acrylate, 4-aminobutyl (meth)acrylate, 6-aminohexyl (meth)acrylate, 2-thioethyl (meth)acrylate, 2-aminoethyl(meth)acrylamide, 2-aminopropyl(meth)acrylamide, 3-aminopropyl(meth) acrylamide, 2-hydroxyethyl(meth)acrylamide, 2-hydroxypropyl(meth)acrylamide or 3-hydroxypropyl(meth)acrylamide. Particular preference is given to 2-hydroxyethyl acrylate, 2-hydroxyethyl methacrylate, 2- or 3-hydroxypropyl acrylate, 1,4-butanediol monoacrylate and 3-(acryloyloxy)-2-hydroxypropyl methacrylate.

Suitable components (c) include compounds containing at least two isocyanate-reactive groups, examples being —OH, —SH, —NH$_2$ and —NHR$^{10}$, wherein R$^{10}$ independently at each occurrence can be hydrogen, methyl, ethyl, iso-propyl, n-propyl, n-butyl, iso-butyl, sec-butyl or tert-butyl.

These compounds are preferably diols or polyols, such as hydrocarbon diols having 2 to 20 carbon atoms, examples being ethylene glycol, 1,2-propanediol, 1,3-propanediol, 1,1-dimethylethane-1,2-diol, 1,6-hexanediol, 1,10-decanediol, bis(4-hydroxycyclo-hexane)isopropylidene, tetramethylcyclobutanediol, 1,2-, 1,3- or 1,4-cyclohexanediol, cyclooctanediol, norbornanediol, pinanediol, decalindiol, etc., esters thereof with short-chain dicarboxylic acids such as adipic acid and cyclohexanedicarboxylic acid, their carbonates, prepared by reacting the diols with phosgene or by transesterification with dialkyl or diaryl carbonates, or aliphatic diamines, such as methylene- and isopropylidene-bis(cyclohexylamine), piperazine, 1,2-, 1,3- or 1,4-diaminocyclohexane, 1,2-, 1,3- or 1,4-cyclohexane-bis(methylamine), etc., dithiols or polyfunctional alcohols, secondary or primary amino alcohols, such as ethanolamine, diethanolamine, monopropanolamine, dipropanolamine, etc., or thioalcohols, such as thioethylene glycol.

Further conceivable compounds include diethylene glycol, triethylene glycol, dipropylene glycol, tripropylene glycol, neopentyl glycol, pentaerythritol, 1,2- and 1,4-butanediol, 1,5-pentanediol, 2-methyl-1,5-pentanediol, 2-ethyl-1,4-butanediol, 1,2-, 1,3- and 1,4-dimethylolcyclohexane, 2,2-bis (4-hydroxycyclohexyl)propane, glycerol, trimethylolethane, trimethylolpropane, trimethylolbutane, dipentaerythritol, ditrimethylolpropane, erythritol and sorbitol, 2-aminoethanol, 3-amino-1-propanol, 1-amino-2-propanol or 2-(2-aminoethoxy)ethanol, bisphenol A, or butanetriol.

Also suitable in addition are unsaturated polyetherols or polyesterols or polyacrylate polyols having an average OH functionality of 2 to 10, and also polyamines, such as polyethylenimine, or polymers containing free amine groups, of poly-N-vinylformamide for example.

Particularly suitable here are the cycloaliphatic diols, such as bis(4-hydroxycyclo-hexane)isopropylidene, tetramethylcyclobutanediol, 1,2-, 1,3- or 1,4-cyclohexanediol, cyclooctanediol or norbornanediol.

The polyurethanes which can be used are obtained by reacting components (a), (b) and (c) with one another.

The molar composition (a):(b):(c) per 3 mol of reactive isocyanate groups in (a) can in general be chosen arbitrarily; preferably it is as follows:

(b) 1.5-3.0, preferably 2.0-2.9, more preferably 2.0-2.5 and in particular 2.0-2.3 mol of isocyanate-reactive groups and (c) 0-1.5, preferably 0.1-1.0, more preferably 0.5-1.0 and in particular 0.7-1.0 mol of isocyanate-reactive groups.

When using the polyurethanes in aqueous systems it is preferable for essentially all of the isocyanate groups present to have undergone reaction.

The formation of the adduct of isocyanate-functional compound and the compound comprising isocyanato-reactive groups takes place generally by mixing the components in any order, at elevated temperature if appropriate. The compound comprising isocynato-reactive groups is preferably added to the isocyanate-functional compound, preferably in two or more steps.

With particular preference the isocyanate-functional compound is introduced to start with and the compounds comprising isocyanate-reactive groups are added. In particular the isocyanate-functional compound (a) is introduced to start with and then (b) is added. Following this it is possible if appropriate for further desired components to be added.

In general the reaction is conducted at temperatures between 5 and 100° C., preferably between 20 to 90° C. and more preferably between 40 and 80° C., and in particular between 60 and 80° C.

It is preferred to operate in this case under anhydrous conditions.

Anhydrous here means that the water content of the reaction system does not amount to more than 5% by weight, preferably not more than 3% by weight and with particular preference not more than 1% by weight.

The reaction can be carried out in the presence of at least one suitable inert gas, an example being nitrogen, argon, helium, carbon dioxide or the like, although this is generally not necessary.

The reaction can also be carried out in the presence of an inert solvent, an example being acetone, iso-butyl methyl ketone, toluene, xylene, butyl acetate or ethoxyethyl acetate.

The urethane (meth)acrylates preferably have a number-average molar weight $M_n$ of 500 to 20 000, in particular 500 to 10 000, more preferably 600 to 3000 g/mol (determined by gel permeation chromatography with tetrahydrofuran and polystyrene as standard).

The urethane (meth)acrylates preferably contain 1 to 5, more preferably 2 to 4 mol of (meth)acrylic groups per 1000 g of urethane (meth)acrylate.

Epoxy (meth)acrylates are obtainable by reacting epoxides with (meth)acrylic acid. Example of suitable epoxides include epoxidized olefins, aromatic glycidyl ethers and aliphatic glycidyl ethers, preferably those of aromatic or aliphatic glycidyl ethers.

Epoxidized olefins may for example be ethylene oxide, propylene oxide, isobutylene oxide, 1-butene oxide, 2-butene oxide, vinyloxirane, styrene oxide or epichlorohydrin, preference being given to ethylene oxide, propylene oxide, isobutylene oxide, vinyloxirane, styrene oxide or epichlorohydrin, particular preference to ethylene oxide, propylene oxide or epichlorohydrin and very particular preference to ethylene oxide and epichlorohydrin.

Aromatic glycidyl ethers are for example bisphenol A diglycidyl ether, bisphenol F diglycidyl ether, bisphenol B diglycidyl ether, bisphenol S diglycidyl ether, hydroquinone diglycidyl ether, alkylation products of phenol/dicyclopentadiene, e.g., 2,5-bis[(2,3-epoxypropoxy)phenyl]octahydro-4,7-methano-5H-indene (CAS No. [13446-85-0]), tris[4-(2,3-epoxypropoxy)phenyl]methane isomers (CAS No. [66072-39-7]), phenol-based epoxy novolaks (CAS No. [9003-354]) and cresol-based epoxy novolaks (CAS No. [37382-79-9]).

Aliphatic glycidyl ethers are for example 1,4-butanediol diglycidyl ether, 1,6-hexanediol dig lycidyl ether, trimethylolpropane trig lycidyl ether, pentaerythritol tetraglycidyl ether, 1,1,2,2-tetrakis[4-(2,3-epoxypropoxy)phenyl]ethane (CAS No. [27043-374]), diglycidyl ethers of polypropylene glycol (α,ω-bis(2,3-epoxypropoxy)poly(oxypropylene)) (CAS No. [16096-30-3]) and of hydrogenated bisphenol A (2,2-bis[4-(2,3-epoxy-propoxy)cyclohexyl]propane, CAS No. [13410-58-7]).

The epoxy (meth)acrylates and epoxy vinyl ethers preferably have a number-average molar weight $M_n$ of 200 to 20 000, more 200 to 10 000 g/mol and very preferably 250 to 3000 g/mol; the amount of (meth)acrylic or vinyl ether groups is preferably 1 to 5, more preferably 2 to 4 per 1000 g of epoxy (meth)acrylate or vinyl ether epoxide (determined by gel permeation chromatography using polystyrene as standard and tetrahydrofuran as eluent).

Carbonate (meth)acrylates comprise on average preferably 1 to 5, preferably 2 to 4, more preferably 2 to 3 (meth)acrylic groups and very preferably 2 (meth)acrylic groups.

The number-average molecular weight $M_n$ of the carbonate (meth)acrylates is preferably less than 3000 g/mol, more preferably less than 1500 g/mol, very preferably less than 800 g/mol (determined by gel permeation chromatography using polystyrene as standard and tetrahydrofuran as solvent).

The carbonate (meth)acrylates are obtainable simply by transesterifying carbonic esters with polyhydric, preferably dihydric, alcohols (diols, e.g., hexanediol) and subsequently esterifying the free OH groups with (meth)acrylic acid or else trarisesterification with (meth)acrylic esters, as described for example in EP-A 92 269. They are also obtainable by reacting phosgene, urea derivatives with polyhydric alcohols, dihydric alcohols for example.

Vinyl ether carbonates are also obtainable, analogously, by reacting a hydroxyalkyl vinyl ether with carbonic esters and also, if appropriate, dihydric alcohols.

Also conceivable are (meth)acrylates or vinyl ethers of polycarbonate polyols, such as the reaction product of the one of the said diols or polyols and a carbonic ester and also a hydroxyl-containing (meth)acrylate or vinyl ether.

Suitable carbonic esters are for example ethylene carbonate, 1,2- or 1,3-propylene carbonate, dimethyl carbonate, diethyl carbonate or dibutyl carbonate.

Suitable hydroxy-containing (meth)acrylates are for example 2-hydroxyethyl (meth)acrylate, 2- or 3-hydroxypropyl (meth)acrylate, 1,4-butanediol mono(meth)acrylate, neopentyl glycol mono(meth)acrylate, glyceryl mono(meth)acrylate and di(meth)acrylate, trimethylolpropane mono (meth)acrylate and di(meth)acrylate and also pentaerythritol mono(meth)acrylate, di(meth)acrylate and tri(meth)acrylate.

Suitable hydroxy-containing vinyl ethers are for example 2-hydroxyethyl vinyl ether and 4-hydroxybutyl vinyl ether.

Particularly preferred carbonate (meth)acrylates are those of formula:

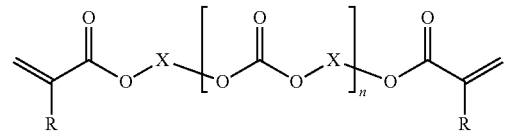

in which R is H or $CH_3$, X is $C_2$-$C_{18}$ alkylene group and n is an integer from 1 to 5, preferably 1 to 3.

R is preferably H and X is preferably $C_2$ to $C_{10}$ alkylene, such as 1,2-ethylene, 1,2-propylene, 1,3-propylene, 1,4-butylene or 1,6-hexylene, for example, more preferably $C_4$ to $C_8$ alkylene. With very particular preference X is $C_6$ alkylene.

The carbonate (meth)acrylates are preferably aliphatic carbonate (meth)acrylates.

Among the polyfunctional polymerizable compounds particular preference is given to urethane (meth)acrylates.

The present invention further provides a radiation-curable coating material comprising at least one compound of formula (I), (II), (III), (V) or (VI),
at least one compound having one or more than one free-radically polymerizable double bond,
if appropriate at least one photoinitiator,
at least one compound having more than one hydroxyl and/or amino group,
if appropriate at least one compound having a hydroxyl or amino group,
if appropriate at least one organometallic tin compound or at least one cesium compound, and
if appropriate further, typical coatings additives.

Photoinitiators can be for example photoinitiators known to the skilled worker, examples being those specified in "Advances in Polymer Science", Volume 14, Springer Berlin 1974 or in K. K. Dietliker, Chemistry and Technology of UV- and EB-Formulation for Coatings, Inks and Paints, Volume 3; Photoinitiators for Free Radical and Cationic Polymerization, P. K. T. Oldring (ed.), SITA Technology Ltd, London.

Suitable examples include mono- or bisacylphosphine oxides as described for example in EP-A 7 508, EP-A 57 474, DE-A 196 18 720, EP-A 495 751 or EP-A 615 980, examples being 2,4,6-trimethylbenzoyidiphenylphosphine oxide (Lucirin® TPO from BASF AG), ethyl 2,4,6-trimethylbenzoylphenylphosphinate (Lucirin® TPO L from BASF AG), bis(2,4,6-trimethylbenzoyl)phenylphosphine oxide (Irgacure® 819 from Ciba Spezialitäctenchemie), benzophenones, hydroxyacetophenones, phenylglyoxylic acid and derivatives thereof, or mixtures of these photoinitiators. Examples that may be mentioned include benzophenone, acetophenone, acetonaphthoquinone, methyl ethyl ketone, valerophenone, hexanophenone, α-phenylbutyrophenone, p-morpholinopropio-phenone, dibenzosuberone, 4-morpholinobenzophenone, 4-morpholinodeoxybenzoin, p-diacetylbenzene, 4-aminobenzophenone, 4'-methoxyacetophenone, β-methyl-anthraquinone, tert-butylanthraquinone, anthraquinonecarboxylic esters, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,4-triacetylbenzene, thioxanthen-9-one, xanthen-9-one, 2,4-dimethylthioxanthone, 2,4-diethylthioxanthone, 2,4-diisopropylthioxanthone, 2,4-dichlorothioxanthone, benzoin, benzoin isobutyl ether, chloroxanthenone, benzoin tetrahydropyranyl ether, benzoin methyl ether, benzoin ethyl ether, benzoin butyl ether, benzoin isopropyl ether, 7H-benzoin methyl ether, benz[de]anthracen-7-one, 1-naphthaldehyde, 4,4'-bis(di-methylamino) benzophenone, 4-phenylbenzophenone, 4-chlorobenzophenone, Michler's ketone, 1-acetonaphthone, 2-acetonaphthone, 1-benzoylcyclohexan-1-ol, 2-hydroxy-2,2-dimethylacetophenone, 2,2-dimethoxy-2-phenylacetophenone, 2,2-diethoxy-2-phenylacetophenone, 1,1-dichloroacetophenone, 1-hydroxyaceto-phenone, acetophenone dimethyl ketal, o-methoxybenzophenone, triphenylphosphine, tri-o-tolylphosphine, benz[a]anthracene-7,12-dione, 2,2-diethoxyacetophenone, benzil ketals, such as benzil dimethyl ketal, 2-methyl-1-[4-(methylthio)phenyl]-2-morpholino-propan-1-one, anthraquinones such as 2-methylanthraquinone, 2-ethylanthraquinone, 2-tert-butylanthraquinone, 1-chloroanthraquinone, 2-amylanthraquinone, and 2,3-butanedione.

Also suitable are nonyellowing or low-yellowing photoinitiators of the phenylglyoxalic ester type, as described in DE-A 198 26 712, DE-A 199 13 353 or WO 98/33761.

Preference among these photoinitiators is given to 2,4,6-trimethylbenzoyldiphenyl-phosphine oxide, ethyl 2,4,6-trimethylbenzoylphenylphosphinate, bis(2,4,6-trimethyl-benzoyl)phenylphosphine oxide, benzophenone, 1-benzoylcyclohexan-1-ol, 2-hydroxy-2,2-dimethylacetophenone and 2,2-dimethoxy-2-phenylacetophenone.

Compounds having more hydroxyl and/or amino group are, for example, the abovementioned polyesterols, polyetherols or polyacrylate polyols.

Polyamines are suitable as well. Amines suitable for this purpose are generally polyfunctional amines of the molar weight range from 32 to 500 g/mol, preferably from 60 to 300 g/mol, which comprise at least two primary, two secondary or one primary and one secondary amino group(s). Examples thereof are diamines such as diaminoethane, diaminopropanes, diaminobutanes, diaminohexanes, piperazine, 2,5-dimethylpiperazine, amino-3-aminomethyl-3,5,5-trimethylcyclohexane (Isophoronediamine, IPDA), 4,4'-diaminodicyclohexylmethane, 1,4-diaminocyclo-hexane, aminoethylethanolamine, hydrazine, hydrazine hydrate or triamines such as diethylene triamine or 1,8-diamino-4-aminomethyloctane or higher amines such as triethylenetetramine, tetraethylenepentamine or polymeric amines such as polyethyleneamines, hydrogenated polyacrylonitriles of at least partly hydrolyzed poly-N-vinylformamides each with a molar weight of up to 2000, preferably up to 1000 g/mol.

For chain termination it is additionally possible in minor amounts to use compounds having one hydroxyl or amino group. They serve primarily to limit the molar weight. Examples of monoalcohols are methanol, ethanol, iso-propanol, n-propanol, n-butanol, isobutanol, sec-butanol, tert-butanol, ethylene glycol monomethyl ether, ethylene glycol monoethyl ether, 1,3-propanediol monomethyl ether, n-hexanol, n-heptanol, n-octanol, n-decanol, n-dodecanol (lauryl alcohol) and 2-ethylhexanol. Examples of monoamines are methylamine, ethylamine, isopropylamine, n-propylamine, n-butylamine, isobutylamine, sec-butylamine, tert-butylamine, n-pentylamine, n-hexylamine, n-heptylamine, n-octylamine, n-decylamine, n-dodecylamine, 2-ethylhexylamine, stearylamine, cetylamine or laurylamine.

As further, typical coatings additives it is possible to make use, for example, of antioxidants, stabilizers, activators (accelerators), fillers, pigments, dyes, antistats, flame retardants, thickeners, thixotropic agents, surfactants, viscosity modifiers, plasticizers or chelating agents.

It is also possible to add one or more thermally activable initiators, such as potassium peroxodisulfate, dibenzoyl peroxide, cyclohexanone peroxide, di-tert-butyl peroxide, azo-bisisobutyronitrile, cyclohexylsulfonyl acetyl peroxide, diisopropyl percarbonate, tert-butyl peroctoate or benzpinacol, and also, for example, those thermally activable initiators which have a half-life at 80° C. of more than 100 hours, such as di-t-butyl peroxide, cumene hydroperoxide, dicumyl peroxide, t-butyl perbenzoate, silylated pinacols, available commercially, for example, under the trade name ADDID 600 from Wacker, or hydroxyl-containing amine N-oxides, such as 2,2,6,6-tetramethylpiperidine-N-oxyl, 4-hydroxy-2,2,6,6-tetramethylpiperidine-N-oxyl etc.

Further examples of suitable initiators are described in "Polymer Handbook", 2nd ed., Wiley & Sons, New York.

Suitable thickeners besides free-radically (co)polymerized (co)polymers include customary organic and inorganic thickeners such as hydroxymethylcellulose or bentonite.

Examples of chelating agents which can be used include ethylenediamineacetic acid and salts thereof and also β-diketones.

Suitable fillers comprise silicates, examples being silicates obtainable by hydrolysis of silicon tetrachloride such as Aerosil® from Degussa, siliceous earth, talc, aluminum silicates, magnesium silicates, calcium carbonates, etc.

Suitable stabilizers comprise typical UV absorbers such as oxanilides, triazines, and benzotriazole (the latter obtainable as Tinuvin® grades from Ciba-Spezialitätenchemie), and benzophenones. They can be used alone or together with suitable free-radical scavengers, examples being sterically hindered amines such as 2,2,6,6-tetramethyl-piperidine, 2,6-di-tert-butylpiperidine or derivatives thereof, e.g., bis(2,2,6, 6-tetramethyl-4-piperidyl) sebacate. Stabilizers are normally used in amounts of from 0.1 to 5.0% by weight, based on the solid components present in the formulation.

The substrates are coated with the coating materials of the invention in accordance with methods which are conventional and are known to the skilled worker, applying at least one coating material of the invention, or coating formulation comprising it, to the target substrate in the desired thickness and drying it if appropriate. This operation can be repeated one or more times as desired. Application to the substrate may be made in a known way, for example, by spraying, troweling, knifecoating, brushing, rolling, roller coating, flow coating, laminating, injection backmolding or coextrusion. The coating composition may also be applied elecrostatically in powder form (powder coatings). The coating thickness is generally in the range from about 3 to 1000 $g/m^2$ and preferably from 10 to 200 $g/m^2$.

Further disclosed is a method of coating substrates which comprises applying a coating material of the invention or coating formulation comprising it, if appropriate with further, typical coatings additives and thermally, chemically or radiatively curable resins, to the substrate and drying it if appropriate, curing it with electron beams or by UV exposure under an oxygenous atmosphere or, preferably, under inert gas, treating it thermally, if appropriate, at temperatures up to the level of the drying temperature, and then treating it thermally at temperatures of up to 160° C., preferably between 60 and 160° C.

The method of coating substrates may also be conducted by following the application of the coating material of the invention, or coating formulation comprising it, first with thermal treatment at temperatures of up to 160° C., preferably between 60 and 160° C., and then with curing using electron beams or by UV exposure under an air atmosphere or, preferably, under inert gas.

Curing of the films formed on the substrate may take place by means of heat alone if desired. Generally, however, the coatings are cured both by exposure to high-energy radiation and thermally.

In addition to or instead of the thermal cure, curing may also take place by means of NIR radiation, which refers here to electromagnetic radiation in the wavelength range from 760 nm to 2.5 μm, preferably from 900 to 1500 nm.

Where two or more films of the coating composition are applied atop one another, it is possible if appropriate for each coating operation to be followed by a thermal, NIR and/or radiation cure.

Examples of suitable radiation sources for the radiation cure include low-pressure, medium-pressure, and high-pressure mercury lamps, fluorescent tubes, pulsed lamps, metal halide lamps, electronic flash installations, which allow radiation curing without photoinitiator, or excimer sources. Radiation curing is accomplished by exposure to high-energy radiation, i.e., UV radiation or daylight, preferably light in the wavelength ($\lambda$) range of from 200 to 700 nm, more preferably from 200 to 500 nm, and very preferably from 250 to 400 nm, or by bombardment with high-energy electrons (electron beams; 150 to 300 keV). Examples of radiation sources used include high-pressure mercury vapor lamps, lasers, pulsed lamps (flash light), halogen lamps, or excimer sources. The radiation dose normally sufficient for crosslinking in the case of UV curing is in the range from 80 to 3000 mJ/cm$^2$.

It is of course also possible to use two or more radiation sources for the cure, e.g., from two to four. These sources may also each emit in different wavelength regions.

Irradiation can be carried out if appropriate in the absence of oxygen as well, such as under an inert gas atmosphere, for example. Suitable inert gases include, preferably, nitrogen, noble gases, carbon dioxide or combustion gases. Irradiation may also take place with the coating material covered with transparent media. Examples of transparent media include polymeric films, glass or liquids, such as water. Particular preference is given to irradiation in the manner described in DE-A 199 57 900.

The invention further provides a method of coating substrates which comprises
i) coating a substrate with a coating material or coating formulation as described above,
ii) removing volatile constituents of the coating material or coating formulation, for the purpose of forming a film, under conditions in which the initiator essentially as yet does not form any free radicals,
iii) if appropriate, irradiating the film formed in step ii) with high-energy radiation, the film being precured, and then, if appropriate, machining the article coated with the precured film or contacting the surface of the precured film with another substrate,
iv) fully curing the film thermally.

Steps iv) and iii) can also be carried out in reverse order, i.e., the film can be cured first thermally and then with high-energy radiation.

ppm and percentage figures used in this specification are by weight unless indicated otherwise.

The examples which follow are intended to illustrate the invention but not to restrict it to these examples.

EXAMPLES

Comparative Example 1

A 250 ml four-necked reaction flask equipped with distillation bridge, Liebig condenser and stirrer was charged with 4.74 g of n-butyl acetate, in which 6.0 g of 2,4,6-tris-(methylcarbamoyl)-1,3,5-triazine, 6.97 g of 2-hydroxyethyl acrylate, 12.5 mg of 4-methoxyphenol, 4 mg of 2,6-di-t-butyl-p-cresol and 0.3 mg of phenothiazine were dissolved, and the solution was brought to an internal temperature of 110° C. The methanol formed was removed by distillation.

Conversion after 300 minutes: 25% of the 2-hydroxyethyl acrylate, 4% of 2,4,6-tris-(2-ethoxyacrylatocarbamoyl)-1,3,5-triazine (HPLC).

Example 1

A 250 ml four-necked reaction flask equipped with distillation bridge, Liebig condenser and stirrer was charged with 12.32 g of n-butyl acetate, in which 6.0 g of 2,4,6-tris-(methylcarbamoyl)-1,3,5-triazine, 6.97 g of 2-hydroxyethyl acrylate, 12.5 mg of 4-methoxyphenol, 4 mg of 2,6-di-t-butyl-p-cresol and 0.3 mg of phenothiazine and also 0.96 mg of cesium acetate were dissolved, and the solution was brought to an internal temperature of 110° C. The methanol formed was removed by distillation.

Conversion after 300 minutes: 50% of the 2-hydroxyethyl acrylate, 17% of 2,4,6-tris-(2-ethoxyacrylatocarbamoyl)-1,3,5-triazine (HPLC).

Example 2

A suspension of 0.136 g of p-methoxyphenol, 0.045 g of di-tert-butyl-p-kresol, 0.003 g of phenothiazine, 0.016 g of dibutyltin dilaurate (DBTL), 2,4,6-trisalkoxycarbamoyl-1,3,5-triazine, diol and/or polyesterol and also hydroxyethyl acrylate (HEA), as indicated in the table, in 30.0 ml of methyl isobutyl ketone (MIBK) was stirred at a bath temperature of 112° C. for 4 hours. Subsequently the reaction mixture was distilled at a bath temperature of 52° C. under a reduced pressure of 750 mbar for 2 hours. This gave a clear resin solution. The molar amounts employed are given in table 2.

Film Tests

The resin solutions were adjusted by adding methyl isobutyl ketone to a viscosity of about 3.5 Pas and were mixed with 4 percent by weight (based on the solids content) of 2-hydroxy-2-methyl-1-phenylpropan-1-one as photoinitiator (Darocur® 1173 from Ciba Spezialitätenchemie). The coating materials were applied using a box-type doctor blade to the respective substrate and dried at 60° C. for 30 minutes to remove the solvent.

The coatings were cured thermally by 30 minutes' heat treatment or exposed under an undoped high-pressure mercury lamp (output 120 W/cm) with a lamp-to-substrate distance of 12 cm and a belt speed of 10 m/min approximately at a temperature of 100° C., or were first exposed and then cured thermally.

The pendulum hardness (PD) was determined in accordance with DIN 53157 and is a measure of the hardness of the coating. The result is reported in seconds until the pendulum comes to a standstill (s). High values in this test denote high hardness. The films for determining the pendulum hardness were applied to glass using a box-type doctor blade. The film thickness prior to curing was 100 μm.

The Erichsen cupping (EC) was determined in accordance with DIN 53156 and is a measure of the flexibility and elasticity. The result is reported in millimeters (mm). High values in this test denote high flexibility. The films for determining the Erichsen cupping were applied to sheet metal using a wire-wound doctor blade. The film thickness prior to curing was 50 μm.

TABLE 1

| Example | 2,4,6-Tris(alkoxy-carbamoyl)-1,3,5-triazine (mol) | HEA (mol) | Diol (mol) | Curing | PD (s) | EC (mm) |
|---|---|---|---|---|---|---|
| 2 | 0.4[1)] | 1.2 | 0.2 A | therm. | 8 | 9.8 |
|   |   |   |   | photochem. | 10 | 9.9 |
|   |   |   |   | photochem. + therm. | 39 | 9.8 |
| 3 | 0.2[1)] | 0.6 | 0.05 A | therm. | 17 | 9.8 |
|   |   |   |   | photochem. | 21 | 9.8 |
|   |   |   |   | photochem. + therm. | 76 | 9.4 |
| 4 | 0.1[1)] | 0.6 | 0.025 A | therm. | 54 | 9.7 |
|   |   |   |   | photochem. | 36 | 7.2 |
|   |   |   |   | photochem. + therm. | 170 | 7.3 |
| 5 | 0.1[2)] | 0.3 | — | therm. | 46 | 5.1 |
|   |   |   |   | photochem. | 200 | 1.2 |
|   |   |   |   | photochem. + therm. | 235 | 2.1 |
| 6 | 0.1[2)] | 0.3 | 0.125 A | therm. | 60 | 9.8 |
|   |   |   |   | photochem. | 83 | 6.1 |
|   |   |   |   | photochem. + therm. | 182 | 1.1 |
| 7 | 0.4[2)] | 1.2 | 0.008 A | therm. | 126 | 5.1 |
|   |   |   |   | photochem. | 153 | 1.1 |
|   |   |   |   | photochem. + therm. | 235 | 3.8 |
| 8 | 0.4[2)] | 1.2 | 0.2 B | therm. | 221 | 3.5 |
|   |   |   |   | photochem. | 161 | 2.3 |
|   |   |   |   | photochem. + therm. | 242 | 2.1 |
| 9 | 0.1[2)] | 0.3 | 6.7 A | therm. | 66 | 4.5 |
|   |   |   | 0.0067 B | photochem. | 129 | 1.1 |
|   |   |   |   | photochem. + therm. | 210 | 1.1 | a) 2,4,6-Tris(methoxycarbamoyl)-1,3,5-triazine
b) 2,4,6-Tris(methoxy/butoxy-carbamoyl)-1,3,5-triazine (molar methyl:butyl ratio = 60:40)
A Polyester formed from 1 mol of adipic acid, 1 mol of isophthalic acid, and 2 mol of 1,6-hexanediol, molar mass about 1000 g/mol
B 1,4-Butanediol The examples show that complete curing is achieved only by combining thermal with photochemical crosslinking. In this way, with the compounds of the invention, extraordinarily hard coatings are obtained.

The invention claimed is:

1. A 1,3,5-triazine carbamate of formula (I)

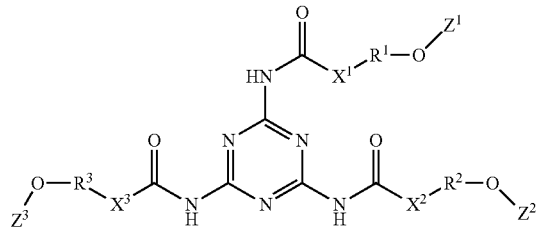

(I)

in which
$R^1$, $R^2$ and $R^3$ each independently of one another are a $C_1$-$C_{20}$ alkylene group,
$X^1$, $X^2$ and $X^3$ each are oxygen, and
$Z^1$, $Z^2$ and $Z^3$ each independently of one another are methacryloyl or acryloyl.

2. A 1,3,5-triazine carbamate of formula (II)

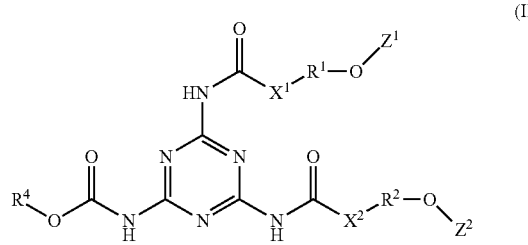

(II)

or of formula (III)

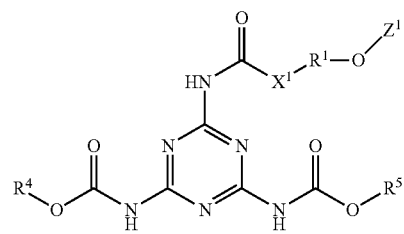

(III)

in which
$R^1$ and $R^2$ each independently of one another are a $C_1$-$C_{20}$ alkylene group,
$X^1$ and $X^2$ each are oxygen,
$Z^1$ and $Z^2$ each independently of one another are methacryloyl or acryloyl, and
$R^4$ and $R^5$ each independently of one another are $C_1$-$C_4$ alkyl.

3. An isocyanato-functional 1,3,5-triazine carbamate of formula (V)

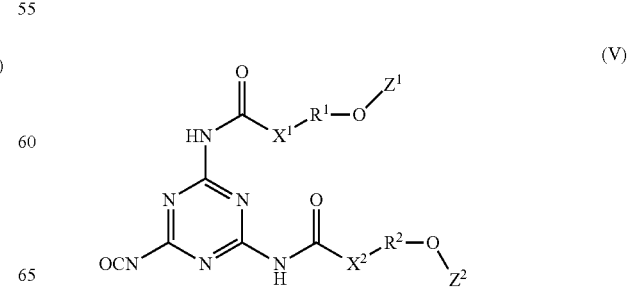

(V)

or formula (VI)

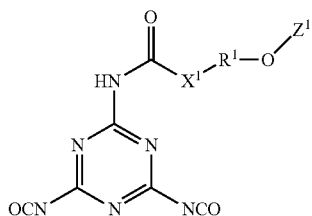
(VI)

in which
R$^1$ and R$^2$ each independently of one another are a C$_1$-C$_{20}$ alkylene group,
X$^1$ and X$^2$ each are oxygen, and
Z$^1$ and Z$^2$ each independently of one another are methacryloyl or acryloyl.

4. A process for preparing a compound of formula (I) of claim 1, comprising:
reacting a compound of formula (IV)

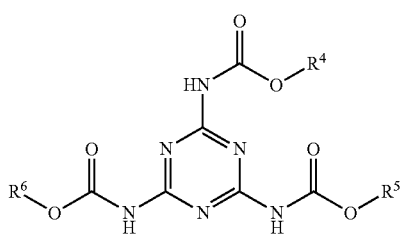
IV in which
R$^4$, R$^5$ and R$^6$ in each case independently of one another can be C$_1$-C$_4$ alkyl,
with at least one alcohol of formula Z$^1$—O—R$^1$—X$^1$—H, Z$^2$—O—R$^2$—X$^2$—H, or Z$^3$—O—R$^3$—X$^3$—H, wherein R$^1$, R$^2$ and R$^3$ each independently of one another are a C$_1$-C$_{20}$ alkylene group, X$^1$, X$^2$ and X$^3$ each are oxygen, and Z$^1$, Z$^2$ and Z$^3$ each independently of one another are methacryloyl or acryloyl.

5. A process for preparing a compound of formula (I), (II) or (III)

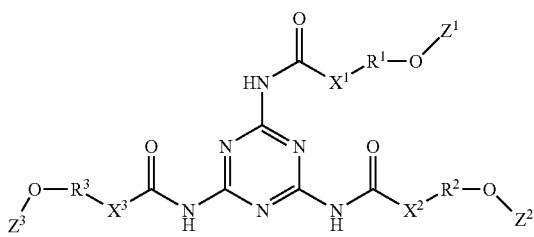
formula (I)

in which
R$^1$, R$^2$ and R$^3$ each independently of one another are a C$_1$-C$_{20}$ alkylene group,
X$^1$, X$^2$ and X$^3$ each are oxygen and
Z$^1$, Z$^2$ and Z$^3$ each independently of one another are methacryloyl or acryloyl;

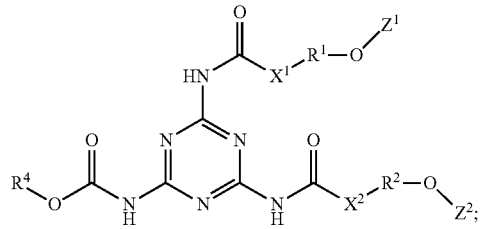
formula (II)

formula (III)

in which
X$^1$, X$^2$, Z$^1$, Z$^2$, R$^1$ and R$^2$ are as defined in formula (I) and R$^4$ and R$^5$ each independently of one another are C$_1$-C$_4$ alkyl,
comprising:
reacting 2,4,6-triisocyanato-1,3,5-triazine with an alcohol of formula Z$^1$—O—R$^1$—X$^1$—H, Z$^2$—O—R$^2$—X$^2$—H, or Z$^3$—O—R$^3$—X$^3$—H and in the case of compound (II) or (III) by simultaneous, prior or subsequent reaction with alcohols of formula R$^4$OH or R$^5$OH, where R$^4$ and R$^5$ each independently of one another can be C$_1$-C$_4$ alkyl.

6. A process for preparing a compound of formula (V)

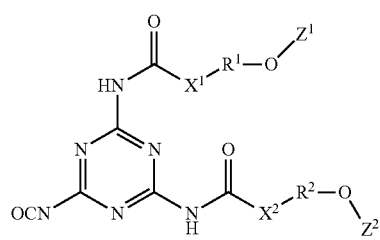
(V)

or formula (VI)

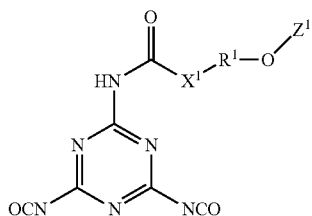
(VI)

in which
R$^1$ and R$^2$ each independently of one another are a C$_1$-C$_{20}$ alkylene group, $X^1$ and $X^2$ each are oxygen and $Z^1$ and $Z^2$ each independently of one another are methacryloyl or acryloyl comprising:

reacting 2,4,6-triisocyanato-1,3,5-triazine with at least one of an alcohol of formula $Z^1$—O—$R^1$—$X^1$—H and an alcohol of formula $Z^2$—O—$R^2$—$X^2$—H.

7. A method comprising:
radiation curing a composition comprising the compound of formula (I) of claim 1.

8. A process for preparing a compound of formula (I) of claim 2, comprising:
reacting a compound of formula (IV)

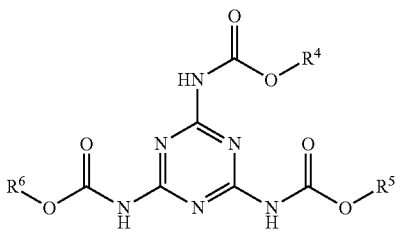

IV in which
$R^4$, $R^5$ and $R^6$ in each case independently of one another can be $C_1$-$C_4$ alkyl,
with at least one alcohol of formula
$Z^1$—O—$R^1$—$X^1$—H or $Z^2$—O—$R^2$—$X^2$—H, wherein $R^1$ and $R^2$ each independently of one another are a $C_1$-$C_{20}$ alkylene group, $X^1$ and $X^2$ each are oxygen, and $Z^1$ and $Z^2$ each independently of one another are methacryloyl or acryloyl.

9. A coating composition, comprising:
one or more of the 1,3,5-triazine carbamate of formula (I) of claim 1.

10. A coating composition, comprising:
one or more of the 1,3,5-triazine carbamate of formulas (II) and (III) of claim 2.

11. A coating composition, comprising:
one or more of the compounds of formulas (V) and (VI):

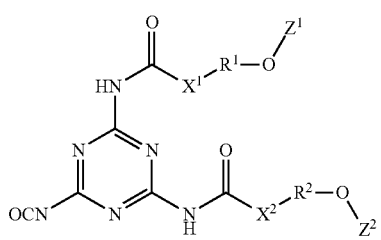

(V)

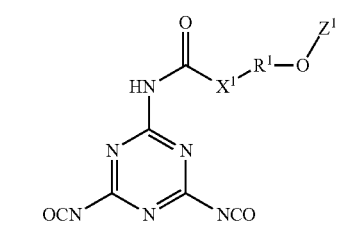

(VI)

in which
$R^1$ and $R^2$ each independently of one another are a $C_1$-$C_{20}$ alkylene group,
$X^1$ and $X^2$ each are oxygen and
$Z^1$ and $Z^2$ each independently of one another are methacryloyl or acryloyl.

12. A method, comprising:
dual-curing a composition comprising one or more of the 1,3,5-triazine carbamate of formula (I) of claim 1.

13. A method, comprising:
dual-curing a composition comprising one or more of the 1,3,5-triazine carbamate of formulas (II) and (III) of claim 2.

14. A method, comprising:
dual-curing a composition comprising one or more of the compounds of formula (V) and (VI) of claim 6.

15. The 1,3,5-triazine carbamate of claim 1, wherein $R^1$, $R^2$ and $R^3$ each independently of one another are selected from the group consisting of 1,2-ethylene, 1,2-propylene, 1,3-propylene, 1,4-butylene, 1,6-hexylene, and 2,2-dimethyl-1,3-propylene.

16. The 1,3,5-triazine carbamate of claim 1, wherein $R^1$, $R^2$ and $R^3$ are the same; and
$Z^1$, $Z^2$ and $Z^3$ are the same.

17. The 1,3,5-triazine carbamate of claim 2, wherein $R^1$, $R^2$ and $R^3$ each independently of one another are selected from the group consisting of 1,2-ethylene, 1,2-propylene, 1,3-propylene, 1,4-butylene, 1,6-hexylene, 2,2-dimethyl-1,3-propylene.

18. The 1,3,5-triazine carbamate of claim 2, wherein $R^1$, $R^2$ and $R^3$ are the same; and
$Z^1$, $Z^2$ and $Z^3$ are the same.

19. The isocyanato-functional 1,3,5-triazine carbamate of claim 3, wherein $R^1$, $R^2$ and $R^3$ each independently of one another are selected from the group consisting of 1,2-ethylene, 1,2-propylene, 1,3-propylene, 1,4-butylene, 1,6-hexylene, 2,2-dimethyl-1,3-propylene.

20. The isocyanato-functional 1,3,5-triazine carbamate of claim 3, wherein $R^1$, $R^2$ and $R^3$ are the same; and
$Z^1$, $Z^2$ and $Z^3$ are the same.

21. The process of claim 4, wherein $R^1$, $R^2$ and $R^3$ each independently of one another are selected from the group consisting of 1,2-ethylene, 1,2-propylene, 1,3-propylene, 1,4-butylene, 1,6-hexylene, and 2,2-dimethyl-1,3-propylene.

22. The process of claim 4, wherein $R^1$, $R^2$ and $R^3$ are the same; and
$Z^1$, $Z^2$ and $Z^3$ are the same.

23. The process of claim 5, wherein $R^1$, $R^2$ and $R^3$ each independently of one another are selected from the group consisting of 1,2-ethylene, 1,2-propylene, 1,3-propylene, 1,4-butylene, 1,6-hexylene, 2,2-dimethyl-1,3-propylene.

24. The process of claim 5, wherein formula (I) $R^1$, $R^2$ and $R^3$ are the same; and
$Z^1$, $Z^2$ and $Z^3$ are the same.

25. The process of claim 6, wherein $R^1$, $R^2$ and $R^3$ each independently of one another are selected from the group consisting of 1,2-ethylene, 1,2-propylene, 1,3-propylene, 1,4-butylene, 1,6-hexylene, and 2,2-dimethyl-1,3-propylene.

26. The process of claim 6, wherein $R^1$, $R^2$ and $R^3$ are the same; and
$Z^1$, $Z^2$ and $Z^3$ are the same.

* * * * *